(12) United States Patent
Liles et al.

(10) Patent No.: US 10,358,529 B2
(45) Date of Patent: Jul. 23, 2019

(54) METHOD OF PREPARING FUNCTIONALIZED PARTICLES

(71) Applicant: Dow Corning Corporation, Midland, MI (US)

(72) Inventors: Donald Taylor Liles, Midland, MI (US); Timothy Andrew Roggow, II, Chesaning, MI (US)

(73) Assignee: DOW SILICONES CORPORATION, Midland, MI (US)

( * ) Notice: Subject to any disclaimer, the term of this patent is extended or adjusted under 35 U.S.C. 154(b) by 0 days.

(21) Appl. No.: 15/534,303

(22) PCT Filed: Dec. 18, 2015

(86) PCT No.: PCT/US2015/066699
§ 371 (c)(1),
(2) Date: Jun. 8, 2017

(87) PCT Pub. No.: WO2016/100830
PCT Pub. Date: Jun. 23, 2016

(65) Prior Publication Data
US 2017/0362390 A1 Dec. 21, 2017

Related U.S. Application Data

(60) Provisional application No. 62/094,605, filed on Dec. 19, 2014.

(51) Int. Cl.
| | | |
|---|---|---|
| C08G 77/38 | (2006.01) | |
| C08J 3/12 | (2006.01) | |
| A61K 8/893 | (2006.01) | |
| C08G 77/12 | (2006.01) | |
| C08G 77/18 | (2006.01) | |
| C08G 77/20 | (2006.01) | |
| C08L 83/04 | (2006.01) | |
| A61K 8/891 | (2006.01) | |
| A61K 8/898 | (2006.01) | |
| A61K 8/899 | (2006.01) | |
| A61Q 19/00 | (2006.01) | |
| C08G 77/388 | (2006.01) | |
| C08G 77/392 | (2006.01) | |
| A61Q 5/02 | (2006.01) | |
| A61Q 11/00 | (2006.01) | |
| A61Q 15/00 | (2006.01) | |
| A61K 8/892 | (2006.01) | |

(52) U.S. Cl.
CPC ............. *C08G 77/38* (2013.01); *A61K 8/891* (2013.01); *A61K 8/892* (2013.01); *A61K 8/893* (2013.01); *A61K 8/898* (2013.01); *A61K 8/899* (2013.01); *A61Q 5/02* (2013.01); *A61Q 11/00* (2013.01); *A61Q 15/00* (2013.01); *A61Q 19/00* (2013.01); *C08G 77/12* (2013.01); *C08G 77/18* (2013.01); *C08G 77/20* (2013.01); *C08G 77/388* (2013.01); *C08G 77/392* (2013.01); *C08J 3/128* (2013.01); *C08L 83/04* (2013.01); *A61K 2800/10* (2013.01); *A61K 2800/412* (2013.01); *A61K 2800/612* (2013.01); *A61K 2800/654* (2013.01); *C08J 2383/04* (2013.01)

(58) Field of Classification Search
CPC .......... C08G 77/12; C08G 77/20; C07F 7/182
See application file for complete search history.

(56) References Cited

U.S. PATENT DOCUMENTS

| | | |
|---|---|---|
| 2,798,053 A | 7/1957 | Brown |
| 3,958,581 A | 5/1976 | Abegg et al. |
| 3,962,418 A | 6/1976 | Birkofer |
| 4,009,256 A | 2/1977 | Nowak, Jr. et al. |
| 4,165,336 A | 8/1979 | Bouillon et al. |
| 4,250,108 A | 2/1981 | Bouillon et al. |
| 4,290,974 A | 9/1981 | Bouillon et al. |

(Continued)

FOREIGN PATENT DOCUMENTS

| | | |
|---|---|---|
| EP | 0114607 A1 | 8/1984 |
| EP | 0487404 A1 | 5/1992 |
| EP | 0518772 A1 | 12/1992 |
| EP | 0518773 A1 | 12/1992 |
| EP | 1074575 A2 | 2/2001 |
| EP | 1266647 A1 | 12/2002 |

(Continued)

OTHER PUBLICATIONS

PCT/US2015/066699 International Search Report dated Dec. 18, 2015, 6 pages.
English language abstract and machine translation for FR2282426 (A2) extracted from http://worldwide.espacenet.com database on May 25, 2017, 14 pages.
English language abstract and machine translation for FR2645148 (A1) extracted from http://worldwide.espacenet.com database on May 25, 2017, 32 pages.

*Primary Examiner* — Kuo Liang Peng
(74) *Attorney, Agent, or Firm* — Warner Norcross & Judd LLP

(57) ABSTRACT

Particles are prepared in an emulsion using a method that includes providing a first reactant having at least two unsaturated carbon-carbon moieties and a second reactant having at least two Si—H moieties, so long as at least one of the unsaturated carbon-carbon moieties of the first reactant or the Si—H moieties of the second reactant is pendant. The method also includes providing a third reactant having a silicon atom and a condensable reactive group bonded to the silicon atom and also having an unsaturated carbon-carbon moiety and/or a Si—H moiety, providing a hydrosilylation catalyst, and providing a polar liquid. The method further includes combining the first, second, and third reactants to form particles that have a cross-linked network wherein the condensable reactive group is disposed on the particles, and adding a silane having an organic moiety and a condensation leaving group to form the particles.

19 Claims, 4 Drawing Sheets

(56) References Cited

U.S. PATENT DOCUMENTS

| | | |
|---|---|---|
| 4,304,730 A | 12/1981 | Bouillon et al. |
| 4,323,549 A | 4/1982 | Bouillon et al. |
| 4,327,031 A | 4/1982 | Bouillon et al. |
| 4,387,089 A | 6/1983 | De Polo |
| 4,406,880 A | 9/1983 | Bouillon et al. |
| 4,489,057 A | 12/1984 | Welters et al. |
| 4,562,067 A | 12/1985 | Hopp et al. |
| 4,585,597 A | 4/1986 | Lang et al. |
| 4,704,272 A | 11/1987 | Oh et al. |
| 4,741,855 A | 5/1988 | Grote et al. |
| 4,775,526 A | 10/1988 | Lang et al. |
| 4,788,006 A | 11/1988 | Bolich, Jr. et al. |
| 4,962,165 A | 10/1990 | Bortnick et al. |
| 5,643,557 A | 7/1997 | Eteve et al. |
| 5,690,915 A | 11/1997 | Eteve et al. |
| 5,690,917 A | 11/1997 | Eteve et al. |
| 5,695,747 A | 12/1997 | Forestier et al. |
| 5,788,955 A | 8/1998 | Eteve et al. |
| 5,795,565 A | 8/1998 | Eteve et al. |
| 5,919,441 A | 7/1999 | Mendolia et al. |
| 5,981,680 A | 11/1999 | Petroff et al. |
| 6,051,216 A | 4/2000 | Barr et al. |
| 6,057,386 A | 5/2000 | Morita et al. |
| 8,084,535 B2 | 12/2011 | Maton et al. |
| 2003/0068348 A1 | 4/2003 | Ferrari et al. |
| 2003/0072730 A1 | 4/2003 | Tournilhac |
| 2003/0170188 A1 | 9/2003 | Ferrari et al. |
| 2003/0232030 A1 | 12/2003 | Lu et al. |
| 2003/0235548 A1 | 12/2003 | Lu et al. |
| 2003/0235552 A1 | 12/2003 | Yu |
| 2003/0235553 A1 | 12/2003 | Lu et al. |
| 2004/0001799 A1 | 1/2004 | Lu et al. |
| 2004/0044121 A1* | 3/2004 | Kadlec .......... A61K 8/891 524/588 |
| 2004/0115153 A1 | 6/2004 | Yu |
| 2004/0115154 A1 | 6/2004 | Yu |
| 2004/0120912 A1 | 6/2004 | Yu |
| 2004/0126336 A1 | 7/2004 | Hansenne et al. |
| 2004/0170586 A1 | 9/2004 | Ferrari et al. |
| 2004/0180032 A1 | 9/2004 | Manelski et al. |
| 2005/0009989 A1 | 1/2005 | Liew et al. |
| 2005/0020769 A1 | 1/2005 | Lu et al. |
| 2005/0089492 A1 | 4/2005 | Lu et al. |
| 2005/0245673 A1 | 11/2005 | Ferrari et al. |
| 2005/0287105 A1 | 12/2005 | Blin et al. |
| 2006/0120983 A1 | 6/2006 | Blin et al. |
| 2006/0204470 A1 | 9/2006 | Tournilhac |
| 2007/0231287 A1 | 10/2007 | Lu |
| 2007/0298256 A1 | 12/2007 | Fukui et al. |
| 2008/0166309 A1 | 7/2008 | McDermott et al. |
| 2008/0254076 A1 | 10/2008 | Ferrari et al. |
| 2009/0269377 A1 | 10/2009 | Lu |
| 2010/0098648 A1 | 4/2010 | Yu |
| 2011/0045963 A1 | 2/2011 | Harimoto |
| 2011/0129431 A1 | 6/2011 | McDermott et al. |
| 2011/0189117 A1 | 8/2011 | Ferrari et al. |

FOREIGN PATENT DOCUMENTS

| | | |
|---|---|---|
| EP | 1266648 A1 | 12/2002 |
| EP | 1266653 A1 | 12/2002 |
| FR | 2236515 A1 | 2/1975 |
| FR | 2282426 A2 | 3/1976 |
| FR | 2326405 A1 | 4/1977 |
| FR | 2430938 A1 | 2/1980 |
| FR | 2440933 A1 | 6/1980 |
| FR | 2592380 A1 | 7/1987 |
| FR | 2645148 A1 | 10/1990 |
| WO | WO9522311 A1 | 8/1995 |
| WO | WO03101412 A2 | 12/2003 |
| WO | WO03105789 A1 | 12/2003 |
| WO | WO03105801 A1 | 12/2003 |
| WO | WO03106614 A2 | 12/2003 |
| WO | WO2004000247 A1 | 12/2003 |
| WO | WO2004020527 A1 | 3/2004 |
| WO | WO2004054523 A1 | 7/2004 |
| WO | WO2004054524 A1 | 7/2004 |
| WO | WO2004060101 A2 | 7/2004 |
| WO | WO2004060271 A2 | 7/2004 |
| WO | WO2004060276 A2 | 7/2004 |

\* cited by examiner ated herein by Stage of International filed on Dec. 18, ll advantages of U.S. 62/094,605 filed on Dec. are incorporated herein by

METHOD OF PREPARING FUNCTIONALIZED PARTICLES

CROSS REFERENCE TO RELATED APPLICATIONS

This application is the National Stage of International Application No. PCT/US2015/066699 filed on Dec. 18, 2015, which claims priority to and all advantages of U.S. Provisional Patent Application No. 62/094,605 filed on Dec. 19, 2014, the contents of which are incorporated herein by reference.

FIELD OF THE DISCLOSURE

The present disclosure generally relates to a method of preparing particles having organic functionality disposed thereon. More specifically, the method utilizes an emulsion, a hydrosilylation reaction, and a condensation reaction to form the cross-linked particles that include organic functionality.

BACKGROUND OF THE DISCLOSURE

It is well known that many organic compounds cannot be utilized in hydrosilylation reactions because of toxic effects on typical hydrosilylation catalysts. For example, nitrogen compounds, amines, quaternary ammonium compounds, and sulfur compounds are known poisons and inhibitors for platinum hydrosilylation catalysts. If used, these compounds can reduce the speed of, or even prevent, hydrosilylation reactions from occurring. For that reason, it can be difficult to form silicones via hydrosilylation that are functionalized with various organic substituents or moieties. Accordingly, there remain opportunities for improvement.

BRIEF DESCRIPTION OF THE FIGURES

Other advantages of the present disclosure will be readily appreciated, as the same becomes better understood by reference to the following detailed description when considered in connection with the accompanying Figure wherein.

SUMMARY OF THE DISCLOSURE

Figure 1:
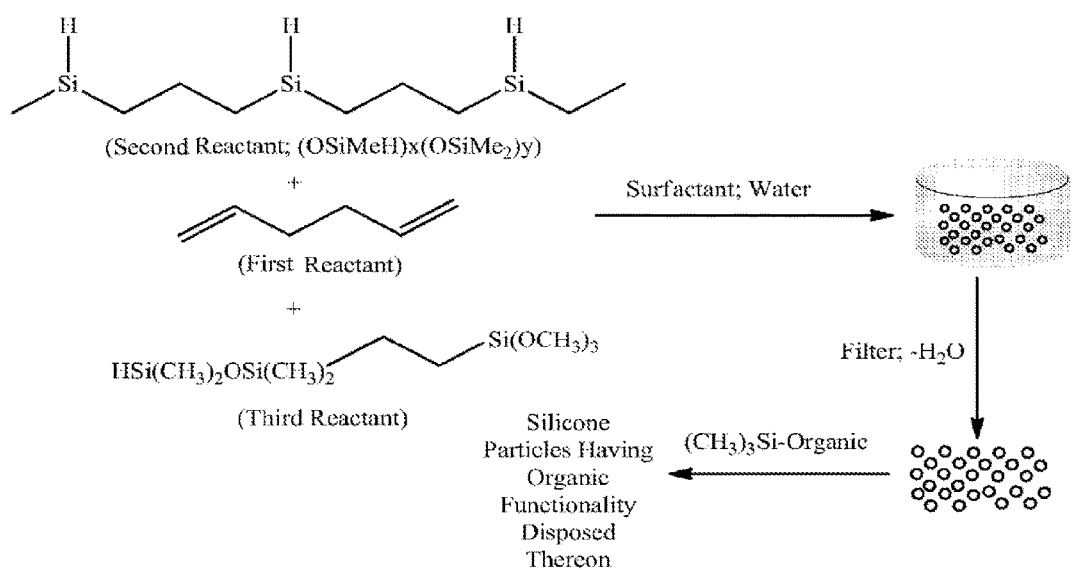
FIG. 1 is a reaction scheme that illustrates one non-limiting embodiment of the method of this disclosure.
Figure 2:
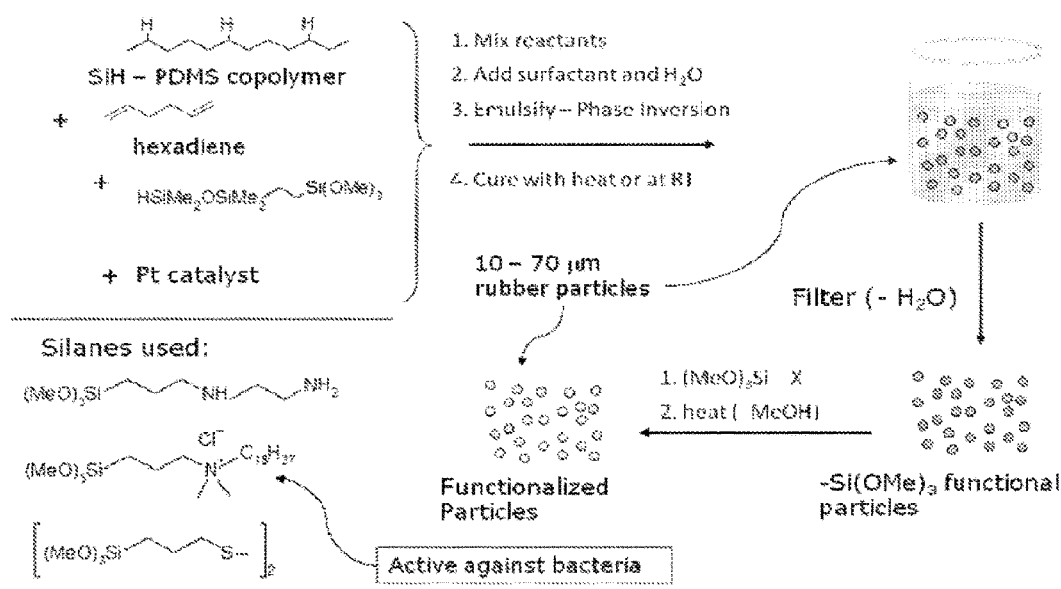
FIG. 2 is another reaction scheme that illustrates an additional non-limiting embodiment of the method of this disclosure.
Figure 3A:
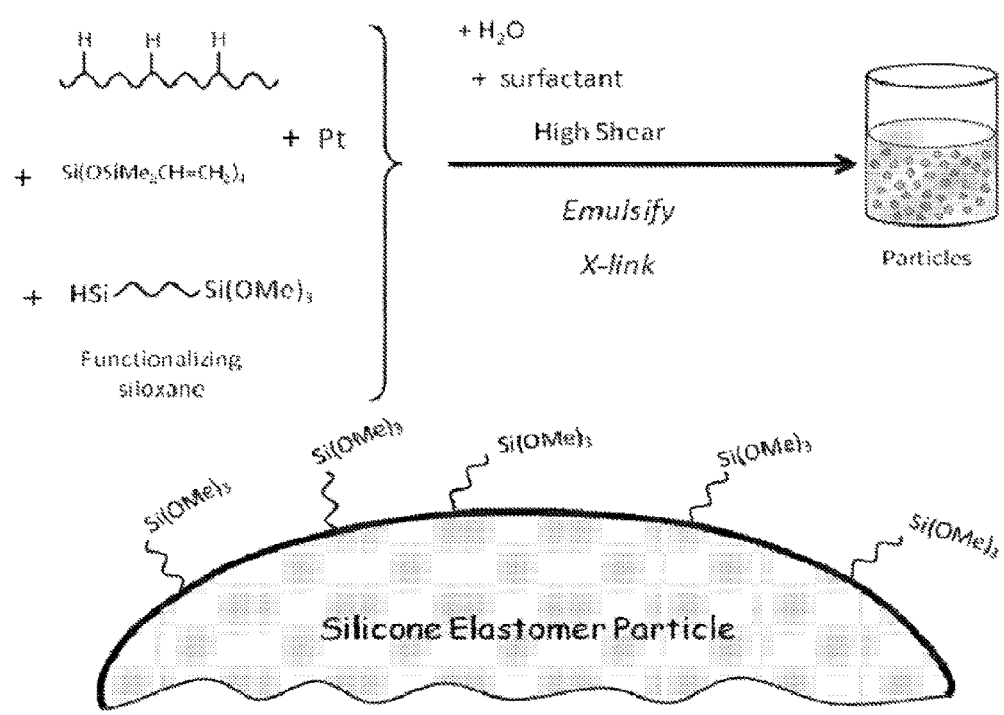
FIG. 3A is an additional reaction scheme that illustrates a first portion of a non-limiting embodiment of the method of this disclosure.
Figure 3B:
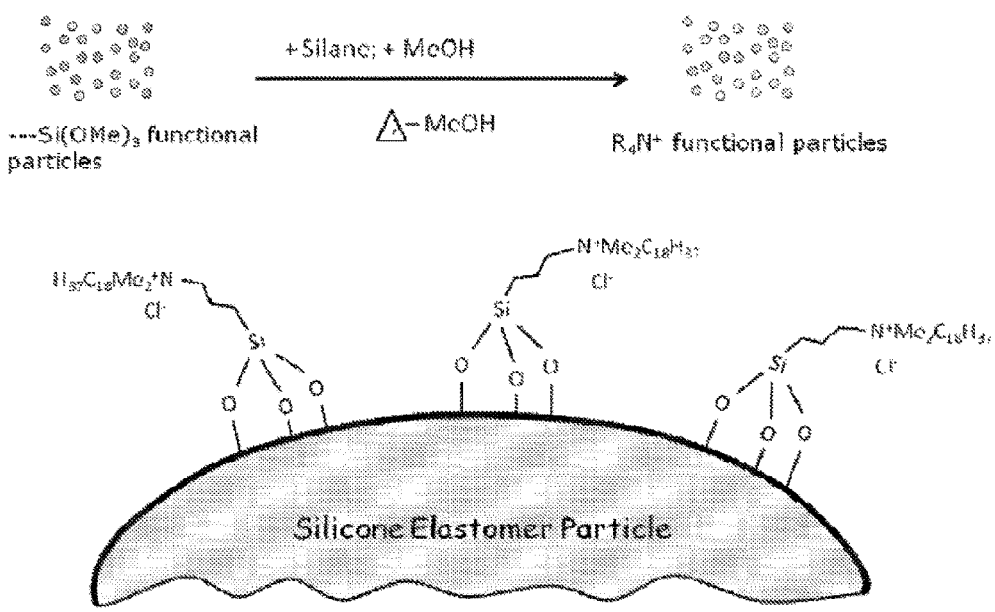
FIG. 3B is a further reaction scheme that illustrates a second portion of a non-limiting embodiment of the method of this disclosure.

This disclosure provides a method of preparing particles in an emulsion wherein the particles have organic functionality disposed thereon. The method includes the steps of providing a first reactant having at least two unsaturated carbon-carbon moieties and providing a second reactant having at least two Si—H moieties, so long as at least one of the unsaturated carbon-carbon moieties of the first reactant or the Si—H moieties of the second reactant is pendant. The method also includes the step of providing a third reactant having a silicon atom and a condensable reactive group bonded to the silicon atom and also having an unsaturated carbon-carbon moiety and/or an Si—H moiety, the step of providing a hydrosilylation catalyst, and the step of providing a polar liquid. The method further includes the step of combining the first, second, and third reactants in the presence of the hydrosilylation catalyst and the polar liquid to form an emulsion wherein the first, second, and third reactants react via a hydrosilylation reaction to form particles in the emulsion that have a cross-linked network wherein the condensable reactive group is disposed on the particles, and wherein the particles are disposed in the polar liquid. Moreover, the method includes the step of adding a silane to the particles wherein the silane has an organic moiety and a condensation leaving group such that the condensable reactive group of the particles reacts with the condensation leaving group of the silane via a condensation reaction to form the particles having the organic functionality disposed thereon.

DETAILED DESCRIPTION OF THE DISCLOSURE

This disclosure provides a method of preparing particles having organic functionality disposed thereon, a dispersion that includes a polar continuous phase and the particles dispersed in the polar continuous phase, and the particles themselves. Each is described in greater detail below.
Method of Preparing the Silicone Particles:
Providing a First Reactant:

The method of preparing the silicone particles (hereinafter described as the "method") includes the step of providing a first reactant having at least two unsaturated carbon-carbon moieties. The step of providing is not particularly limited and may be alternatively described as supplying, purchasing, delivering, making available, etc. The first reactant is typically provided to a reactor or other reaction vessel, as is described in greater detail below.

The first reactant is also not particularly limited and may be organic or inorganic. The first reactant may be organic (e.g. and free of silicon atoms), may be a silane or siloxane or combinations thereof, or may be inorganic and still include the unsaturated carbon-carbon moiety. The first reactant may have two or more than two unsaturated carbon-carbon moieties. A combination of compounds may also be utilized wherein one or more compounds of the combination each independently include a single unsaturated carbon-carbon moiety and one or more other compounds of the combination each independently include two or more unsaturated carbon-carbon moieties.

Each of the at least two (or each) unsaturated carbon-carbon moieties may independently be an alkynyl moiety (i.e., a carbon-carbon triple bond; C≡C) or an alkenyl moiety (i.e., a carbon-carbon double bond; C=C). For example, the first reactant may include one or more alkynyl moieties and one or more alkenyl moieties simultaneously. Alternatively, the first reactant may include two or more alkenyl moieties and no alkynyl moieties. Even further, the first reactant may include two or more alkynyl moieties and no alkenyl moieties.

In one embodiment, the first reactant is organic. In another embodiment, the first reactant is chosen from alkenes having 3, 4, 5, 6, 7, 8, 9, 10, 11, or 12, carbon atoms. In various embodiments, the first reactant is hexadiene or octadiene or a combination thereof.

Alternatively, the first reactant may be a silane or siloxane. In still other embodiments, the first reactant is a siloxane cross linker. In another embodiment, the first reactant is a siloxane having two or more unsaturated organic groups such as vinyl or allyl groups. In still another embodiment, the first reactant is $Si(OSi(CH_3)_2CH=CH_2)_4$. Alternatively, the first reactant may be $Si(CH=CH_2)_4$; $CH_3Si(CH=CH_2)_3$; $(OSiCH_3CH=CH_2)_n$, wherein n is 3-6; and/or $H_2C=CHMe_2SiOSiMe_2CH=CH_2$. The first reactant may also be $—(OSiMe_2)_x(OSiMeCH=CH_2)_y—$, wherein x is greater than 1 and less than 1,000, e.g. ~10, and y is greater than 2 and less than 10,000, e.g. ~100. The first reactant can also be endcapped with any endcapping moieties known in the art such as trimethyl groups on silicon atoms, e.g. $(CH_3)_3Si$.

If the first reactant is a combination of compounds, then each may independently be as described above. Each of the at least two unsaturated carbon-carbon moieties may be located at a terminal position or an internal (pendant) position on the first reactant. The first reactant may be alternatively described as a cross-linker due to the presence of two or more unsaturated carbon-carbon moieties. However, and as described below, a minimum of five reactive groups are present, and/or the sum of the number of the unsaturated carbon-carbon moieties of the first reactant and the Si—H moieties of a second reactant is at least five and/or at least one of the unsaturated carbon-carbon moieties or the Si—H moieties of a second reactant must be pendant so that cross-linking can occur. In other words, all of the reactive moieties cannot be terminal because then a linear product would form and not a cross-linked product.

The first reactant is typically provided in an amount of from 0.1 to 1.0, from 1 to 10, or from 10 to 100, parts by weight per 100 parts by weight of the second reactant, as described below. If the first reactant is a combination of compounds, then a total weight of the combination is typically present in an amount as immediately described above. In additional embodiments, any value, or range of values, both whole and fractional, within or between any one or more values described above are contemplated.

Providing a Second Reactant:

The method also includes the step of providing a second reactant having at least two Si—H moieties. The step of providing may be as described above or may be different. The second reactant may be such that the only silicon atoms present in the second reactant are of the Si—H moieties, e.g. an organic compound having at least two Si—H moieties. Alternatively, the second reactant may include more than two silicon atom which may or may not be part of the at least two Si—H moieties. Alternatively, the second reactant may be a silane, siloxane, or combination thereof, having an Si—H moiety.

The second reactant has two or more Si—H moieties. A combination of compounds may also be utilized wherein one or more compounds of the combination each independently include a single Si—H moiety and one or more other compounds of the combination each independently include at least two Si—H moieties.

Each of the at least two Si—H moieties may be located at a terminal position or an internal (pendant) position on the second reactant if the second reactant is a linear polymer chain. Each Si—H moiety may be located at a terminal position or an internal (pendant) position. However, and as described below, a minimum of five reactive groups are present, and/or the sum of the number of the unsaturated carbon-carbon moieties of the first reactant and the Si—H moieties of a second reactant is at least five and/or at least one of the unsaturated carbon-carbon moieties or the Si—H moieties of the second reactant must be pendant so that cross-linking can occur. In other words, all of the reactive moieties cannot be terminal because then a linear product would form and not a cross-linked product. The at least two unsaturated carbon-carbon moieties and at least two Si—H moieties allow cross-linking to occur.

In various embodiments, the second reactant is dimethylhydrogen terminated polysiloxane (fluid) such as $H(CH_3)_2Si(OSi(CH_3)_2)_nOSi(CH_3)_2H$, wherein n is 5-1,000. Alternatively, the second reactant is a methyl hydrogen polysiloxane such as $(OSiMeH)_x(OSiMe_2)_y$, wherein x is greater than 1 and less than 1,000, e.g. ~10, and y is greater than 2 and less than 10,000, e.g. ~100. The second reactant can also be endcapped with any endcapping moieties known in the art such as trimethyl groups on silicon atoms, e.g. $(CH_3)_3Si$.

In one embodiment, the first reactant is an organopolysiloxane or organic compound (free of silicon atoms) having an average of at least two alkenyl groups and the second reactant is an organopolysiloxane or organic compound that has an average of at least two silicon-bonded hydrogen atoms (but is free from other silicon atoms).

The second reactant is typically provided in an amount of from 1000 to 100 or from 100 to 10, parts by weight per 1 part by weight of the first reactant. If the second reactant is a combination of compounds, then a total weight of the combination is typically present in an amount as immediately described above. In additional embodiments, any value, or range of values, both whole and fractional, within or between any one or more values described above are contemplated.

Providing a Third Reactant:

The method also includes the step of providing a third reactant having a silicon atom and a condensable reactive group bonded to the silicon atom and also having an unsaturated carbon-carbon moiety and/or an Si—H moiety. In one embodiment, the third reactant has both an unsaturated carbon-carbon moiety and an Si—H moiety. In another embodiment, both the unsaturated carbon-carbon moiety and the Si—H moiety are not present, i.e., in this embodiment, the third reactant does not include both types of moieties and only includes one or the other. The step of providing may be as described above or may be different.

The third reactant is also not particularly limited and may act as a chain stopper. If a chain stopper, the third reactant cannot include more than one unsaturated carbon-carbon moiety or Si—H moiety. Said differently, in such an embodiment, the third reactant may include only one unsaturated carbon-carbon moiety or only one Si—H moiety, but not both the unsaturated carbon-carbon moiety and the Si—H moiety. If a chain stopper, the third reactant cannot include two or more unsaturated carbon-carbon moieties, two or more Si—H moieties, or two or more unsaturated carbon-carbon moieties and two or more Si—H moieties. The single unsaturated carbon-carbon moiety may be terminal or pendant. The single Si—H moiety may be terminal or pendant. However, in the alternative, the third reactant may be described as a cross-linker that has both an unsaturated carbon-carbon moiety and an Si—H moiety, or more than one carbon-carbon moiety and/or more than one Si—H moiety.

The unsaturated carbon-carbon moiety, or the Si—H moiety, of the third reactant may be any of those as described above relative to the first reactant. However, the unsaturated carbon-carbon moiety, or the Si—H moiety, of the third reactant may be the same or may be different from those described above of the first and second reactants.

The condensable reactive group of the third reactant is not particularly limited except that this group is capable of participating in a condensation reaction, as appreciated in the art, and is bonded to a silicon atom of the third reactant. The silicon atom bonded to the condensable reactive group is not the same as the silicon atom of the Si—H group, if that group is utilized. For example, the condensable reactive group (or leaving group) may be an alkoxy group, an oxime group, a carboxy group, an acetoxy group, an alkyleneoxy group, an amine group, an aminoxy group, or an amide group. Alternatively, the condensable reactive group may be any group appreciated by those of skill in the art as an acceptable leaving group on silicon that can function in a condensation reaction.

In one embodiment, the third reactant has the formula:

$$X_m R'_n Si(OR)_{1-3}$$

wherein m is 1-10, each of R' and R is independently an organic radical having 1-12 carbon atoms, X is independently the unsaturated carbon-carbon moiety or the Si—H moiety. Each of R' and R can independently be an organic radical each having 1, 2, 3, 4, 5, 6, 7, 8, 9, 10, 11, or 12 carbon atoms.

In other embodiments, the third reactant has one of the following formulae: $CH_2$=$CHSi(Me)_2OSi(Me)_2RSi(OMe)_3$, $SiHRSi(OMe)_3$, or $(OSiMeH)_x(OSiMeOR)_y$ wherein x+y is 3 to 8 and there is at least 1 Si—H and 1 SiOR per molecule, and wherein R is an organic radical having from 1, 2, 3, 4, 5, 6, 7, 8, 9, 10, 11, or 12 carbon atoms. In various embodiments, the third reactant can be cyclic and have Si—H and SiOMe (or SiOR) in the same molecule. In other embodiments, the third reactant is all $(OSiMeH)_n$ wherein some of the Si—H is substituted with SiOMe and n is 3 to 8.

Moreover, the third reactant can include two or more compounds wherein each is defined by the aforementioned formula. In other embodiments, the third reactant is $H_2C$=$CHSi(OCH_3)_3$, $HMe_2Si(CH_2)_2SiMe_2OSi(OMe)_3$ or $HSi(OCH_2CH_3)_3$, or a combination thereof.

In still another embodiment, the condensable reactive group of the third reactant is further defined as an alkoxy group. Alternatively, the condensable reactive group may be an —Si(OR) group wherein R is an organic radical having 1-12 carbon atoms, i.e., 1, 2, 3, 4, 5, 6, 7, 8, 9, 10, 11, or 12, carbon atoms or any range of values thereof.

A combination of third reactants may also be utilized wherein one or more compounds of the combination each independently include one unsaturated carbon-carbon moiety or one Si—H moiety and others include more than one.

The third reactant is typically provided in an amount of from 0.01 to 0.1, from 0.1 to 1, or from 1 to 50, parts by weight per 100 parts by weight of the first reactant. If the third reactant is a combination of compounds, then a total weight of the combination is typically present in an amount as immediately described above. In additional embodiments, any value, or range of values, both whole and fractional, within or between any one or more values described above are contemplated.

Providing a Hydrosilylation Catalyst:

The method also includes the step of providing a hydrosilylation catalyst. The step of providing may be the same as described above or may be different. The hydrosilylation catalyst may be any known in the art and may be utilized as an aqueous emulsion. In various embodiments, the hydrosilylation catalyst includes platinum, rhodium, iridium, palladium or ruthenium, or combinations thereof. The hydrosilylation catalyst may be, for example, a fine platinum powder, platinum black, chloroplatinic acid, an alcoholic solution of chloroplatinic acid, an olefin complex of chloroplatinic acid, a complex of chloroplatinic acid and alkenylsiloxane, or a thermoplastic resin that includes the aforementioned platinum catalyst. In another embodiment, the hydrosilylation catalyst is platinum vinyl siloxane complex such as Karstedt's catalyst, or Speier's catalyst, or combinations thereof. The hydrosilylation catalyst may be a single catalyst or a combination of two or more catalysts. In other words, one, more than one, or at least one, hydrosilylation catalysts may be utilized.

The hydrosilylation catalyst is typically provided in an amount of from 1 to 100, 1 to 10, or 10 to 100, parts per million of platinum calculated as elemental platinum based on total particle weight. In additional embodiments, any value, or range of values, both whole and fractional, within or between any one or more values described above are contemplated.

Providing a Polar Liquid:

The method further includes the step of providing a polar liquid. Typically, the polar liquid is not a "solvent" in that the first, second, and third reactants do not typically "dissolve" in the polar liquid. The polar liquid is not particularly limited but may be described as a hydrophilic liquid, a polar aprotic liquid, or a polar protic liquid. Typically, the terminology "hydrophilic" describes that the polar liquid is polar and/or (a) protic and is water loving, as understood in the art. The polar liquid may be, include, consist essentially of, or consist of water, alcohols, polar protic liquids, polar aprotic liquids, and combinations thereof. Various non-limiting examples of the polar liquid include water, alcohols, tetrahydrofuran (THF), ethyl acetate, acetone, dimethylformamide (DMF), acetonitrile, dimethyl sulfoxide (DMSO), formic acid, n-butanol, isopropanol (IPA), nitromethane, ethanol, methanol, acetic acid, and combinations thereof. In various embodiments, the polar liquid is chosen from methanol, ethanol, glycols, glycol ethers, water, and combinations thereof. Alternatively, the polar liquid may be chosen from methanol, ethanol, propanol, butanol, and/or any other alkane based alcohol solvents. In various embodiments, the polar liquid is water or methanol or ethanol or propanol or butanol or a glycol or an alkane based alcohol solvent or a combination of two or more of these. The water is not particularly limited and may be tap water, well water, potable or non-potable water, etc. The water may be purified or non-purified. The terminology "consisting essentially of" typically describes that the continuous phase (or water itself) includes less than 10, 9, 8, 7, 6, 5, 4, 3, 2, 1, 0.5, or 0.1, weight percent of a hydrophobic or non-polar liquid. In various embodiments, one, more than one, or at least one, polar liquid may be utilized.

The polar liquid is typically provided in an amount of from 20 to 80, 25 to 75, 30 to 70, 35 to 65, 40 to 60, 45 to 55, or about 50, parts by weight per 100 parts by weight of the continuous phase, described in greater detail below. In additional embodiments, any value, or range of values, both whole and fractional, within or between any one or more values described above are contemplated.

Combining the First, Second, and Third Reactants:

The method further includes the step of combining the first, second, and third reactants. More typically, this step is further defined as combining the first, second, and third reactants, along with the hydrosilylation catalyst and the polar liquid. As first introduced above, the first, second, and third reactant are typically provided or introduced into a reactor or other reaction vessel. The first, second, and third reactants are combined in the presence of the hydrosilylation catalyst and the polar liquid to form an emulsion wherein the polar liquid is the continuous phase and the first, second, and third reactants are the dispersed phase. Typically, this emulsion is described as an oil in water emulsion (i.e., an o/w emulsion).

The first, second, and third reactants, along with the hydrosilylation catalyst and the polar liquid, may each be independently combined or introduced into the reaction vessel in a continuous mode or a batch mode. The first, second, and third reactants, along with the hydrosilylation catalyst and the polar liquid, may be combined in any order and in one or more discrete steps. Alternatively, first, second, and third reactants, along with the hydrosilylation catalyst and the polar liquid, may be combined with any one or more of each other simultaneously.

In one embodiment, the step of combining the first, second, and third reactants further comprises phase inverting the combination of the first, second, and third reactants (e.g. in the presence of the hydrosilylation catalyst and polar liquid) to form the emulsion. However, the step of forming the emulsion is not limited and may also or alternatively include applying shear, mixing, vortexing, and/or any other method known in the art.

The method may also include the steps of providing a surfactant and/or combining the surfactant with one or more of the first, second or third reactants, with the hydrosilylation catalyst, with the polar liquid, and/or with any one or more of these, either sequentially or simultaneously. The surfactant may be chosen from non-ionic surfactants, cationic surfactants, anionic surfactants, amphoteric surfactants, and combinations thereof. Suitable non-ionic surfactants include, but are not limited to, Guerbet alcohol alkoxylates (or derivatives thereof), alkylphenol alkoxylates, ethoxylated and propoxylated fatty alcohols, alkyl polyglucosides and hydroxyalkyl polyglucosides, sorbitan derivatives, N-alkylglucamides, alkylene oxide block copolymers such as block copolymers of ethylene oxide, propylene oxide and/or butylene oxide, polyhydroxy and polyalkoxy fatty acid derivatives, amine oxides, silicone polyethers, various polymeric surfactants based on polysaccharides, polymeric surfactants based on polyvinyl alcohol and polyacrylamide, polyoxyalkylene copolymers, and combinations thereof.

Suitable cationic surfactants include, but are not limited to, interface-active compounds including ammonium groups such as alkyldimethylammonium halides and compounds having the chemical formula RR'R"R"'N+X— wherein R, R', R", and R"' are independently selected from the group of alkyl groups, aryl groups, alkylalkoxy groups, arylalkoxy groups, hydroxyalkyl(alkoxy) groups, and hydroxyaryl(alkoxy) groups and wherein X is an anion.

Suitable anionic surfactants include, but are not limited to, fatty alcohol sulfates and sulfates of ethoxylated fatty alcohols. Further non-limiting examples of suitable anionic surfactants include alkanesulfonates, linear alkylbenzenesulfonates, linear alkyltoluenesulfonates, diphenyl sulfonates, and diphenylether sulfonates. Still further, the anionic surfactant may include olefinsulfonates and di-sulfonates, mixtures of alkene- and hydroxyalkane-sulfonates or di-sulfonates, alkyl ester sulfonates, sulfonated polycarboxylic acids, alkyl glyceryl sulfonates, fatty acid glycerol ester sulfonates, alkylphenol polyglycol ether sulfates, paraffinsulfonates, alkyl phosphates, acyl isothionates, acyl taurates, acyl methyl taurates, alkylsuccinic acids, alkenylsuccinic acids and corresponding esters and amides thereof, alkylsulfosuccinic acids and corresponding amides, mono- and di-esters of sulfosuccinic acids, acyl sarcosinates, sulfated alkyl polyglucosides, alkyl polyglycol carboxylates, hydroxyalkyl sarcosinates, and combinations thereof. Still further, polymeric anionic surfactants based on acrylic acid or sulfonated polystyrene, and combinations thereof, may also be used. Suitable ampholytic surfactants include, but are not limited to, aliphatic derivatives of secondary and/or tertiary amines which include an anionic group, betaine derivatives, and combinations thereof.

Additionally, the surfactant may independently include or be aliphatic and/or aromatic alkoxylated alcohols, LAS (linear alkyl benzene sulfonates), paraffin sulfonates, FAS (fatty alcohol sulfates), FAES (fatty alcohol ethersulfates), alkylene glycols, trimethylolpropane ethoxylates, glycerol ethoxylates, pentaerythritol ethoxylates, alkoxylates of bisphenol A, and alkoxylates of 4-methylhexanol and 5-methyl-2-propylheptanol, and combinations thereof. Further, the surfactant may include or be alkylpolysaccharides including linear or branched alkyl groups, linear or branched alkenyl groups, alkylphenyl groups, alkylene groups, and/or combinations thereof.

The one or more surfactants may be used in amounts of from 0.01 to 20, 1 to 15, 1 to 10, 1 to 5, 5 to 20, 5 to 15, 5 to 10, 10 to 20, 10 to 15, 0.01 to 5, 0.05 to 5, 0.1 to 5, 0.1 to 4, 0.1 to 3, 0.1 to 2, 0.1 to 1, 0.5 to 5, 0.5 to 4, 0.5 to 3, 0.5 to 2, 0.5 to 1, 1 to 5, 1 to 4, 1 to 3, 1 to 2, 2 to 5, 2 to 4, 2 to 3, 3 to 5, 3 to 4, or 4 to 5, weight percent based on a total weight of the first, second, and third reactants (e.g. the weight of the dispersed phase)

Upon combination to form the emulsion and in the presence of the hydrosilylation catalyst, the first, second, and third reactants may react at ambient temperature or may fail to react at ambient temperature. The emulsion may require heating to promote the hydrosilylation reaction or to speed up the hydrosilylation reaction. Alternatively, no heating may be required or desired. For example, the emulsion and/or one or more of the first, second, and third reactants or the polar liquid may be heated to temperatures from room temperature (approximately 25° C.) to 250° C., alternatively from room temperature to 150° C., alternatively from room temperature to 115° C., at atmospheric pressure. The reactants may be heated for a length of time sufficient to cure (cross-link) the reactants, e.g. from 0.1 to 3 hrs.

Typically, the hydrosilylation reaction proceeds between the unsaturated carbon-carbon moieties of the first reactant and the Si—H moieties of the second reactant, as is generally understood in the art. This reaction forms a cross-linked network. Accordingly, the particles, at this point, have a cross-linked network. The cross-linked network may be further described as a cross-linked silicone network or a cross-linked organic (i.e., non-silicone) network.

The third reactant may or may not act as a chain stopper to stop the growing chain formed from the aforementioned hydrosilylation reaction. Any one or more of these reactions may occur simultaneously or sequentially. The condensable reactive group of the third reactant is typically not involved in the aforementioned hydrosilylation reactions of the first, second, and third reactants.

Upon the hydrosilylation reaction of the first, second, and third reactants, particles are formed. In other words, the first, second, and third reactants react in the presence of the hydrosilylation catalyst and in the emulsion to form the particles via one or more hydrosilylation reactions to form the particles in the emulsion. Alternatively, the particles may be present in a slurry.

In various embodiments, the particles are typically further defined as silicone or polyorganosiloxane particles. Typically, if the first, second, and/or third reactants include silicon-oxygen or siloxane bonds, the particles may be described as silicone or polyorganosiloxane particles.

However, the particles could be alternatively described as organic particles that include a particular weight or molar percent of silicon. Typically, if the first, second, and third reactants include very little weight or molar percent of silicon, the particles will be mostly organic. Typically, the particles must include some weight or molar percent of silicon because the second reactant includes the at least two Si—H moieties. In other words, the particles are not entirely organic and free of silicon because at least some silicon atoms are present due to the Si—H moieties of the second reactant.

At this stage, the particles can be alternatively described as the hydrosilylation reaction product of the first, second, and third reactants. The particles may be described as elastomeric such that they are insoluble, but swellable, in a solvent.

The particles formed in the aforementioned reactions have the condensable reactive group disposed thereon and are disposed in the polar liquid. If the particles are solid particles, then upon formation of the particles in the polar liquid, the aforementioned emulsion may be more accurately described as a dispersion wherein the polar liquid is the continuous phase and the (solid) particles are the dispersed phase that is dispersed in the continuous phase. However, if the particles are not solid (e.g. are a gel or liquid) then the aforementioned emulsion may continue to be accurately described as an emulsion wherein the polar liquid is the continuous phase and the (non-solid, e.g. gel or liquid) particles are the dispersed phase that is dispersed in the continuous phase.

Alternatively, the particles formed in this stage of the method may be described as (silicone elastomeric or organic polymeric) particles that include Si-alkoxy groups chemically bonded to a polymer network of the particles. However, the aforementioned particles that are formed at this stage of the method are not the final particles because the particles formed at this stage of the method are yet to be further functionalized. In other embodiments, the particles formed from this step of the method may be described as having —Si(OR)$_n$ groups wherein R may be as described herein or be any organic moiety and n is a number of from 1 to 6, i.e., 1, 2, 3, 4, 5, or 6. These groups may be described as being covalently bonded to a polymeric network formed upon reaction of the first, second, and third reactants.

Removing the Polar Liquid:

The method may optionally include the step of removing the polar liquid from the particles or separating the polar liquid from the particles. In one embodiment, if the polar liquid is methanol and/or ethanol, the polar liquid may be removed or may be allowed to remain. The method may include the step of filtering, drying, spray drying, lyophilizing, or desiccating the particles. Alternatively, the method may be free of the step of removing or separating the polar liquid from the particles.

In one embodiment, the polar liquid is water and the method includes the step of removing the water from the particles and drying the particles. In another embodiment, the polar liquid is methanol and/or ethanol and the method includes the step of removing the methanol and/or ethanol from the particles and drying the particles. In still another embodiment, the polar liquid is methanol and/or ethanol (each of which may be combined with water) and the method does not include the step of removing the methanol and/or ethanol. In an alternative embodiment, the polar liquid may be water and the method does not include the step of removing the water. In other words, the particles may be allowed to remain in the polar liquid or may be removed therefrom.

It is also contemplated that a portion of the polar liquid may be removed and a portion of the polar liquid may be allowed to remain. For example, if the polar liquid is removed, it may be removed in any amount. For example, an entirety of the polar liquid may be removed or any portion less than the entirety of the polar liquid may be removed. The polar liquid may be removed by any mechanism known in the art. For example, the polar liquid may be removed by vacuum and/or filtration (e.g. vacuum filtration), evaporation, desiccation, heating in an oven, centrifugation, spray drying, freeze drying, and the like.

Combining the Particles with a Silane:

The method even further includes the step of combining the particles with a silane. The particles may be combined with the silane while the particles remain dispersed in the polar liquid or while the particles are in a dry or partially dry form. Similarly, the silane may be combined with the particles while the silane is in a solid, neat, or diluted form. In one embodiment, the silane is combined with a diluent or solvent that dilutes the silane to improve efficiency of combination with the particles. The diluent or solvent is not particularly limited but is typically a hydrophilic or polar liquid, as described above. In various embodiments, the diluent or solvent is methanol, or ethanol, or a glycol, or water, or a combination thereof. In still another embodiment, the diluents or solvent is any of the polar liquids described above. It is also contemplated that the particles and the silane may be combined to form a slurry. Alternatively, the particles may be in slurry prior to combination with the silane.

The silane that is combined with the particles has an organic moiety and also has a condensation leaving group. A single silane may be used or a combination of silanes may be used. In other words, one, more than one, or at least one, silane may be utilized. The organic moiety may be any known in the art and is not particularly limited. In various embodiments, the organic moiety includes one or more nitrogen, sulfur, oxygen, and/or phosphorous atoms. The organic moiety includes carbon atoms but is not limited to total number. For example, the organic moiety may include 1 to 40, 2 to 39, 3 to 38, 4 to 37, 5 to 36, 6 to 35, 7 to 34, 8 to 33, 9 to 32, 10 to 31, 11 to 30, 12 to 29, 13 to 28, 14 to 27, 15 to 26, 16 to 25, 17 to 24, 18 to 23, 19 to 22, 20, or 21 carbon atoms. The organic moiety may be or include linear, branched, or cyclic (portions) and may be or include aromatic or non-aromatic (portions). In various embodiments, the organic moiety is chosen from alkanes, alkenes, alkynes, carboxylates, benzene, toluenes, haloalkanes, alcohols (e.g. hydroxyl groups), ketones, aldehydes, acyl halides, carbonates, carboxylates, carboxylic acids, esters, peroxides, ethers, hemiacetals, hemiketals, acetals, ketals, orthoesters, orthocarbonate esters, amides, amines, imines, imides, isocyanates, azides, azo compounds, cyanates, nitrates, nitriles, nitrites, nitro compounds, nitroso compounds, pyridyl groups, thiols, sulfides, disulfides, sulfoxides, sulfones, sulfinic acid groups, sulfonic acid groups, thiocyanates, thiones, thials, phosphines, phosphonic acid groups, phosphates, phosphodiesters, and combinations thereof. In additional embodiments, the organic moiety is chosen from amino, quaternary ammonium, mercapto, disulfide, and tetrasulfide groups, and combinations thereof. The organic moiety is typically present in a weight percent of 0.01, 0.10, 0.25, 0.50, 1, 5, 10, or 25 based on a total weight of the particles.

Alternatively, the silane may be a methoxy- and/or ethoxy-functional silane. In one embodiment, the silane includes nitrogen. In another embodiment, the silane includes sulfur. In a further embodiment, the silane includes nitrogen and sulfur.

In one embodiment, the silane may have a formula $R_1Si(R_2O)_3$, wherein $R_1$ is independently selected from the group consisting of the organic moiety containing polar compound such as nitrogen or sulfur and $R_2$ is independently selected from the group consisting of hydrogen, methyl and methoxy and ethoxy and alkoxy.

In other embodiments, the silane is chosen from i-$C_4H_9$Si(OMe)$_3$, n-$C_8H_{17}$Si(OEt)$_3$, (MeO)$_3$Si(CH$_2$)$_3$NH(CH$_2$)$_2$NH$_2$, (MeO)$_3$Si(CH$_2$)$_3$NH$_2$, (EtO)$_3$Si(CH$_2$)$_3$NH$_2$, (MeO)$_3$Si(CH$_2$)$_3$NMe$_2$, (MeO)$_3$Si(CH$_2$)$_3$N$^+$Me$_2$C$_{18}$H$_{37}$$^-$Cl, (MeO)$_3$Si(CH$_2$)$_3$N$^+$Me$_3$$^-$Cl and (MeO)$_3$Si(CH$_2$)$_3$SH, and combinations thereof.

The condensation leaving group of the silane is also not particularly limited except that it is capable of being a leaving group during a condensation reaction, as is understood in the art. For example, the condensation leaving group maybe an alkoxy group, an oxime group, a carboxy group, an acetoxy group, an alkyleneoxy group, an amine group, or an amide group, or combinations thereof. The condensation leaving group may be the same or different from the condensable reactive group described above. The condensation leaving group is typically present in a weight percent of 0.1 to 10 based on a total weight of the particles.

Upon combination of the particles and the silane, the condensable reactive group of the particles reacts with the condensation leaving group of the silane via a condensation reaction to form the silicone particles having the organic functionality disposed thereon. A condensation reaction is typically a stepwise reaction in which two or more reactants yield a single main product with accompanying formation of water or of some other small molecule, e.g. ammonia, ethanol, acetic acid, hydrogen sulfide. Typically, the mechanism of a condensation reaction includes consecutive addition and elimination reactions. However, the condensation reaction of this disclosure is not particularly limited and may proceed by any mechanism known in the art. Typically, this reaction occurs at room temperature or upon heating, for example, at temperatures from room temperature (approximately 25° C.) to 150° C. or any value or range of values therebetween.

Relative to the condensation reaction, a condensation catalyst may be used or may be omitted. For example, a condensation catalyst may be used along with heat or without heating. Further, heat alone may be used to effect a condensation reaction.

For example, the method may also include the step of adding the condensation catalyst to the first, second, and/or third reactants and/or to the particles in the emulsion and/or to the silane such that the condensable reactive group of the particles reacts with the condensation leaving group of the silane via the condensation reaction. This reaction can proceed by any known condensation reaction. The condensation catalyst and the hydrosilylation catalyst may be added together or one before the other. For example, the condensation catalyst and the hydrosilylation catalyst may be combined and/or added to the first, second, and/or third reactants prior to hydrosilylation. In one embodiment, the condensation catalyst is present during hydrosilylation (though inactive) and later catalyzes the condensation reaction.

Similarly, the condensation catalyst is not particularly limited and may be any known in the art. In various embodiments, the condensation catalyst is dibutyltin dilaurate, dibutyltin diacetate, dimethyltin dineodecanoate, stannous octoate, stannous oleate, stannous neodecanoate, dioctyltindilaurate, stannous bis-2-ethylhexanoate, iron octoate, zinc octoate, and the like, and combinations thereof. Alternatively, guanidines such as tetramethylguanidine, and amine salts of carboxylic acids such as triethylammonium acetate, can also be used. The amount of the condensation catalyst utilized herein is also not particularly limited. In various embodiments, the condensation catalyst is utilized in amounts of from 0.1 to 10, 0.1 to 1, 1 to 10, 0.1, 0.2, 0.3, 0.4, 0.5, 0.6, 0.7, 0.8, 0.9, 1, 2, 3, 4, 5, 6, 7, 8, 9, or 10, parts by weight per 100 parts by weight of the particles. Although the condensation reaction may proceed at room temperature, heat may be applied. In additional embodiments, any value, or range of values, both whole and fractional, within or between any one or more values described above are contemplated.

In another embodiment, the condensation catalyst is formed into an emulsion with water and the emulsion is added to the particles.

In one embodiment, the condensation catalyst is diluted in a diluent, e.g. any of those described above or a diluent that is different. In a related embodiment, the step of adding the condensation catalyst is further defined as combining the particles with the condensation catalyst diluted in the diluent. The diluent is not particularly limited and may be chosen from methanol, ethanol, glycols, water, and combinations thereof.

Additional Embodiments:

This disclosure also provides a method of preparing the particles wherein the method includes the aforementioned steps of providing the first reactant, providing the second reactant, providing the third reactant, providing the hydrosilylation catalyst, and providing the polar liquid. However, in this embodiment, the method includes a means for forming the silicone particles having the organic functionality disposed thereon. For example, the means for forming the silicone particles may be any one or more steps described above, in whole or in part, and in any combination.

Cross-Linked Particles:

The silicone particles themselves ultimately formed using the method of this disclosure have the organic functionality disposed thereon, as described above. The particles may be alternatively described as a plurality of particles. The particles may be a solid, liquid, or elastomer, e.g. silicone rubber which is known in the art as an elastomeric compound that has both solid and liquid properties. The particles may be described as elastomeric. For example, the particles may be further defined as silicone rubber that is not dissolvable (or minimally soluble, as understood in the art) in an organic solvent. The silicone rubber may also be described as swellable in one or more organic solvents. Alternatively, the silicone particles may be described as polyorganosiloxane particles or particles that are, include, consist essentially of, or consist of, one or more polyorganosiloxanes, or one or more silicones, or one or more silicone rubbers, etc. Alternatively, the silicone particles may be described as particles that are, include, consist essentially of, or consist of, the aforementioned hydrosilylation reaction product of the first, second, and third reactants. In various embodiments, the terminology "consisting essentially of" describes that the silicone particles are free of, or include less than 10, 9, 8, 7, 6, 5, 4, 3, 2, 1, 0.5, 0.1, or 0.05, weight percent of one or more organic polymers and/or non-silicone polymers.

In various embodiments, the silicone particles have a silicone core and an organic moiety covalently bonded to the core. The core may be a liquid or solid, as described above. The core may be solid or hollow. Typically, the core is, includes, consists essentially of, or consists of, the hydrosilylation reaction product of the first, second, and third reactants, as described above. The core may be this hydrosilylation reaction product and not include any other compounds therein. For example, the core may be described as a solid core that does not include any inner core of any material that is not the aforementioned hydrosilylation reaction product. In various embodiments, the terminology "consists essentially of" describes that the core is free of, or includes less than 10, 9, 8, 7, 6, 5, 4, 3, 2, 1, 0.5, 0.1, or 0.05, weight percent of one or more organic polymers and/or non-silicone polymers.

The organic moiety is covalently bonded to the silicone core via a condensation reaction of the condensable reactive group of the third reactant and the condensation leaving group of the aforementioned silane. More specifically, the organic moiety is typically bonded to a surface of the silicone core by covalent bonds formed from the condensation reaction of the condensable reactive groups (from the third reactant) that were available for reaction at the surface of the core. The core itself may include a portion of the organic moiety therein. For example, the organic moiety may penetrate the surface of the core and/or may be external to the surface of the core. An inside of the core may also include the organic moiety that is not covalently bonded via the condensation reaction. In addition, the inside of the core may include unreacted or partially reacted condensable reactive groups that did not react with, and/or were not exposed to, the condensation leaving group of the silane. In addition, it is contemplated that one or more condensable reactive groups may remain on the surface of the core and fail to react with the condensation leaving group of the silane for kinetic, thermodynamic and/or steric reasons.

Referring back to the particles themselves, the particles are not particularly limited in size or shape. Typically, the particles are approximately spherical or oval shaped, as understood by those of skill in the art. The particles may have an average diameter (or a distribution of average diameters) of from 0.1 to 1,000, 1 to 500, 1 to 450, 1 to 400, 1 to 350, 1 to 300, 1 to 250, 1 to 200, 1 to 150, 1 to 100, 100 to 500, 150 to 450, 200 to 400, 250 to 350, 300 to 350, 5 to 95, 10 to 90, 15 to 85, 20 to 80, 25 to 75, 30 to 70, 35 to 65, 40 to 60, 45 to 55, 50 to 55, 1 to 20, 2 to 19, 3 to 18, 4 to 17, 5 to 16, 6 to 15, 7 to 14, 8 to 13, 9 to 12, 10 to 11, 1 to 10, 2 to 9, 3 to 8, 4 to 7, 5 to 6, 2 to 10, 3 to 9, 4 to 8, 5 to 7, 5 to 6, 50 to 70, 55 to 65, or 60 to 65, microns. The average diameter of the particles may be determined using any known particle size instrument such as a Malvern Mastersizer® S or, in some cases, using optical microscopy and/or scanning electron microscopy.

Moreover, the silicone particles may include one or more additives including, but not limited to preservatives, biocides, thickeners, freeze/thaw additives, rust inhibitors, pigments, and other additives known in the art.

It is contemplated that the particles ultimately formed from the method, i.e., the particles that have the organic functionality disposed thereon and are formed from combination with the aforementioned silane may share one or more properties with the particles that are formed earlier in the method via the step of combining the first, second, and third reactants in the presence of the hydrosilylation catalyst and the polar liquid to form an emulsion wherein the first, second, and third reactants react via hydrosilylation to form particles that have the condensable reactive group disposed thereon and that are disposed in the polar liquid. However, the particles that are ultimately formed from this method have the organic functionality disposed thereon while the particles formed earlier in the method do not have this organic functionality disposed thereon. Nevertheless, apart from the organic functionality, the particles ultimately formed and the particles formed earlier in the method may both be as described above. For example, both may be a solid, liquid, or elastomer, e.g. silicone rubber which is known in the art as an elastomeric compound that has both solid and liquid properties. Both may be described as elastomeric. Both may be described as polyorganosiloxane particles or particles that are, include, consist essentially of, or consist of, one or more polyorganosiloxanes, or one or more silicones, or one or more silicone rubbers, etc. Both may be described as particles that are, include, consist essentially of, or consist of, the aforementioned hydrosilylation reaction product of the first, second, and third reactants. In various embodiments, the terminology "consisting essentially of" describes that the silicone particles are free of, or include less than 10, 9, 8, 7, 6, 5, 4, 3, 2, 1, 0.5, 0.1, or 0.05, weight percent of one or more organic polymers and/or non-silicone polymers.

In addition, both may have the same or a similar core and only differ by the organic moiety or functionality bonded to the core. For example, both may have a liquid or solid core. The core of both may be solid or hollow and may be, include, consist essentially of, or consist of, the hydrosilylation reaction product of the first, second, and third reactants, as described above. The core of both may be this hydrosilylation reaction product and not include any other compounds therein. The core of both may be described as a solid core that does not include any inner core of any material that is not the aforementioned hydrosilylation reaction product. In various embodiments, the terminology "consists essentially of" describes that the core of both is free of, or includes less than 10, 9, 8, 7, 6, 5, 4, 3, 2, 1, 0.5, 0.1, or 0.05, weight percent of one or more organic polymers and/or non-silicone polymers.

The organic functionality may be any in the art and may be any of the organic moieties described above. For example, the organic functionality may be amino, quaternary ammonium, mercapto, disulfide, and tetrasulfide functionality, or combinations thereof.

The particles may be used in an emulsion, slurry, or dispersion and/or may be dried and used as a powder. Alternatively, the polar liquid of the emulsion, slurry, or dispersion may be removed such that the liquid particles form an oil.

The particles, emulsion, slurry, and/or dispersion may be utilized in any product such as personal care products (e.g. shampoos, deodorants, anti-dandruff products, oral care compositions, and the like), in anti-bacterial products, in anti-acne products, in wound-care products, in anti-fungal products (e.g. in foot powders or lotions or sprays), in coatings, in cosmetics, in textiles, and the like. Depending on the organic functionality of the particles, the particles, emulsion, slurry, and/or dispersion may exhibit anti-bacterial or anti-microbial properties. Alternatively, the particles, emulsion, slurry, and/or dispersion may exhibit anti-static or water-repellant properties.

Dispersion:

This disclosure also provides a dispersion that includes a polar continuous phase and the aforementioned silicone particles disposed in the polar continuous phase. As described above, if the particles are solid, the dispersion includes the solid particles dispersed in the (liquid) polar continuous phase. If the particles are liquid, the dispersion is typically further defined as an emulsion wherein the liquid particles are dispersed in the (liquid) polar continuous phase. The dispersion may be alternatively described as a slurry. The dispersion or emulsion, as described herein or as described above, may include a surfactant or one or more surfactants, as described above.

Personal Care Composition:

This disclosure also provides a personal care composition, which may also be described as a personal care product composition. The personal care composition includes the particles of this disclosure. The personal care composition may be in the form of a cream, a gel, a powder, a paste, or a freely pourable liquid. Generally, such compositions can be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition may be functional with respect to the portion of the body to which it is applied, cosmetic, therapeutic, or some combination thereof. Conventional examples of such products include, but are not limited to, antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care composition may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Suitable carriers are appreciated in the art. In one embodiment, the personal care composition is a deodorant, a skin care composition, a hair care composition, a wound care composition, or an oral care composition.

The personal care composition can be used in or for a variety of personal, household, and healthcare applications. In particular, the particles of the present disclosure may be used in the personal care products as described in U.S. Pat. Nos. 6,051,216, 5,919,441, 5,981,680; WO 2004/060271 and WO 2004/060101; in sunscreen compositions as described in WO 2004/060276; in cosmetic compositions also containing film-forming resins, as described in WO 03/105801; in the cosmetic compositions as described in US Pat. App. Pub. Nos. 2003/0235553, 2003/0072730 and 2003/0170188, in EP Pat. Nos. 1,266,647, 1,266,648, and 1,266,653, in WO 03/105789, WO 2004/000247 and WO 03/106614; as additional agents to those described in WO 2004/054523; in long wearing cosmetic compositions as described in US Pat. App. Pub. No. 2004/0180032; and/or in transparent or translucent care and/or make up compositions as described in WO 2004/054524, all of which are expressly incorporated herein by reference in various non-limiting embodiments.

The particles can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the particles may be used in a conventional manner for example for conditioning the skin. An effective amount of the particles may be applied to the skin. Such effective amounts generally are from 1 mg/cm$^2$ to 3 mg/cm$^2$. Application to the skin typically includes working the particles into the skin. This method for applying to the skin typically includes the steps of contacting the skin with the particles in an effective amount and then rubbing the particles into the skin. These steps can be repeated as many times as desired to achieve the desired benefit.

Use of the particles on hair may use a conventional manner for conditioning hair. An effective amount of the particles for conditioning hair is applied to the hair. Such effective amounts generally are from 1 g to 50 g, typically from 1 g to 20 g. Application to the hair typically includes working the particles through the hair such that most or all of the hair is contacted with the particles. This method for conditioning the hair typically includes the steps of applying an effective amount of the particles to the hair, and then working the particles through the hair. These steps can be repeated as many times as desired to achieve the desired conditioning benefit.

Non-limiting examples of additives which may be formulated into the particles include, but are not limited to, additional silicones, anti-oxidants, cleansing agents, colorants, additional conditioning agents, deposition agents, electrolytes, emollients and oils, exfoliating agents, foam boosting agents, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, waxes, rheology-modifying agents, anti-dandruff, anti-acne, anti-carie and wound healing-promotion agents.

The personal care composition, such as a shampoo or cleanser, may include at least one anionic detersive surfactant. This can be any of the well-known anionic detersive surfactants typically used in shampoo formulations. These anionic detersive surfactants can function as cleansing agents and foaming agents in the shampoo compositions. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Typically, the detersive surfactant is chosen from sodium lauryl sulfate, ammonium lauryl sulfate, triethanolamine lauryl sulfate, sodium lauryl ether sulfate, and ammonium lauryl ether sulfate. The anionic detersive surfactant can be present in the shampoo composition in an amount from 5 to 50 wt % and typically 5 to 25 wt % based on the total weight of the shampoo composition.

The personal care composition may include at least one cationic deposition aid, typically a cationic deposition polymer. The cationic deposition aid is typically present at levels of from 0.001 to 5%, typically from 0.01 to 1%, more typically from 0.02% to 0.5% by weight. The cationic deposition polymer may be a homopolymer or be formed from two or more types of monomers. The molecular weight of the cationic deposition polymer is typically from 5,000 to 10,000,000, typically at least 10,000 and typically from 100,000 to 2,000,000. The cationic deposition polymers typically have cationic nitrogen containing groups such as quaternary ammonium or protonated amino groups, or a combination thereof. The cationic charge density has been found to need to be at least 0.1 meq/g, typically above 0.8 or higher. The cationic charge density should not exceed 4 meq/g, it is typically less than 3 and more typically less than 2 meq/g. The charge density can be measured using the Kjeldahl method and is within the above limits at the desired pH of use, which will in general be from 3 to 9 and typically from 4 to 8. It is contemplated that any and all values or ranges of values between those described above may also be utilized. The cationic nitrogen-containing group is typically present as a substituent on a fraction of the total monomer units of the cationic deposition polymer. Thus when the cationic deposition polymer is not a homopolymer it can include spacer noncationic monomer units. Such cationic deposition polymers are described in the CTFA Cosmetic Ingredient Directory, 3rd edition, which is expressly incorporated herein by reference in one or more non-limiting embodiments. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers typically have C1-C7 alkyl groups, more typically C1-C3 alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are typical. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g. alkyl vinyl imidazolium, alkyl vinyl pyridinium, alkyl vinyl pyrrolidine salts. The alkyl portions of these monomers are typically lower alkyls such as the C1-C7 alkyls, more typically C1 and C2 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are typically C1-C7 hydrocarbyls, more typically C1-C3, alkyls. The cationic deposition aids can include combinations of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g. Chloride salt) (referred to in the industry by the Cosmetic, Toiletry, and Fragrance Association, "CTFA" as Polyquaternium-16) such as those commercially available from BASF Wyandotte Corp. (Parsippany, N.J., USA) under the LUVIQUAT tradename (e.g. LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g. GAFQUAT 755N); cationic diallyl quaternary ammonium-containing polymer including, for example, dimethyl diallylammonium chloride homopolymer and copolymers of acrylamide and dimethyl diallylammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in UK Application No. 9403156.4 (WO95/22311), each of which is expressly incorporated herein in one or more non-limiting embodiments. Other cationic deposition aids that can be used include polysaccharide polymers, such as cationic cellulose derivatives and cationic starch derivatives. Cationic polysaccharide polymer materials suitable for use in compositions of the disclosure include those of the formula: $A-O(R-N^+R^1R^2R^3X^-)$ wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^1$, $R^2$, $R^3$) typically being 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g. as described in U.S. Pat. No. 3,958,581), each of which is expressly incorporated herein by reference in one or more non-limiting embodiments.

The personal care composition may include a foam boosting agent. A foam boosting agent is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting agent. The foam boosting agent is typically chosen from fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Typically a foam boosting agent is chosen from lauric acid diethanolamide, N-lauryl dimethylamine oxide, coconut acid diethanolamide, myristic acid diethanolamide, and oleic acid diethanolamide. The foam boosting agent is typically present in the shampoo compositions in an amount from 1 to 15 wt % and more typically 2 to 10 wt % based on the total weight of the composition. The composition may further include a polyalkylene glycol to improve lather performance. Concentration of the polyalkylene glycol in the shampoo composition may be from 0.01% to 5%, typically from 0.05% to 3%, and more typically from 0.1% to 2%, by weight of the shampoo composition. The optional polyalkylene glycols are characterized by the general formula: $H(OCH_2CHR)_n$—OH wherein R is chosen from H, methyl, and combinations thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from 1500 to 25,000, typically from 2500 to 20,000, and more typically from 3500 to 15,000. Polyethylene glycol polymers useful herein are PEG-2M wherein R equals H and n has an average value of 2,000 (PEG-2M is also known as Polyox WSR9N-10, which is available from Union Carbide and as PEG-2,000); PEG-5M wherein R equals H and n has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of 7,000 (PEG-7M is also known as Polyox WSRO N-750 available from Union Carbide); PEG-9M wherein R equals H and n has an average value of 9,000 (PEG 9-M is also known as Polyox WSRS N-3333 available from Union Carbide); and PEG-14 M wherein R equals H and n has an average value of 14,000 (PEG-14M is also known as Polyox WSRO N-3000 available from Union Carbide). Other useful polymers include the polypropylene glycols and mixed polyethylene/polypropylene glycols.

The personal care composition may include a suspending agent at concentrations effective for suspending a silicone conditioning agent, or other water-insoluble material, in dispersed form in the personal care composition. Such concentrations may be from 0.1% to 10%, typically from 0.3% to 5.0%, by weight of the personal care composition. Suspending agents include crystalline suspending agents which can be categorized as acyl derivatives, long chain amine oxides, and combinations thereof, concentrations of which can be from 0.1% to 5.0%, typically from 0.5% to 3.0%, by weight of the shampoo compositions. These suspending agents are described in U.S. Pat. No. 4,741,855, which is expressly incorporated herein by reference in one or more non-limiting embodiments. These typical suspending agents include ethylene glycol esters of fatty acids typically having from 16 to 22 carbon atoms. More typical are the ethylene glycol stearates, both mono and distearate, but particularly the distearate containing less than 7% of the mono stearate. Other suitable suspending agents include alkanol amides of fatty acids, typically having from 16 to 22 carbon atoms, more typically 16 to 18 carbon atoms, typical examples of which include stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitate, etc.); glyceryl esters (e.g. glyceryl distearate) and long chain esters of long chain alkanol amides (e.g. stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the typical materials listed above may be used as suspending agents. For example, it is contemplated that suspending agents with long chain hydrocarbyls having C8-C22 chains may be used. Other long chain acyl derivatives suitable for use as suspending agents include N,N-dihydrocarbyl amido benzoic acid and soluble salts thereof (e.g. Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g. stearyl dimethyl amine oxide. Other suitable suspending agents include xanthan gum at concentrations ranging from 0.3% to 3%, typically from 0.4% to 1.2%, by weight of the shampoo compositions. The use of xanthan gum as a suspending agent is described, for example, in U.S. Pat. No. 4,788,006, which is expressly incorporated herein by reference in one or more non-limiting embodiments. Combinations of long chain acyl derivatives and xanthan gum may also be used as a suspending agent in the shampoo compositions. Such combinations are described in U.S. Pat. No. 4,704,272, which is expressly incorporated herein by reference in one or more non-limiting embodiments. Other suitable suspending agents include carboxyvinyl polymers. Typical among these polymers are the copolymers of acrylic acid crosslinked with polyallylsucrose as described in U.S. Pat. No. 2,798,053, which is expressly incorporated herein by reference in one or more non-limiting embodiments. Examples of these polymers include Carbopol 934, 940, 941, and 956, available from B.F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow) phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g. methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition may include one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care composition may include one or more oils independent from the carrier fluid described above. The term "oil" as used herein describes any material which is substantially insoluble in water. Suitable oils include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate and silicones especially cyclomethicone and dimethicone and combinations thereof. Suitable low viscosity oils have a viscosity of 5 to 100 mPA·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity surface oils generally have a viscosity of 200-1,000,000 mPA·s at 25° C., typically a viscosity of 100,000-250,000 mPA·s. Surface oils include castor oil, lanolin and lanolin derivatives, triisocetyl citrate, sorbitan sesquioleate, 010-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof. The suggested ratio of low viscosity to high viscosity oils in the oil phase is 1:15 to 15:1, typically 1:10 to 10:1 respectively. The typical formulation of the disclosure includes 1 to 20% of a combination of low viscosity and high viscosity surface oils.

Mineral oils, such as liquid paraffin or liquid petroleum, or animal oils, such as perhydrosqualene or arara oil, or alternatively of vegetable oils, such as sweet almond, calophyllum, palm, castor, avocado, jojaba, olive or cereal germ oil, may be utilized. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition may include various waxes. The waxes generally have a melting point of from 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or combinations thereof. In one embodiment, the personal care composition includes 10-30% of a combination of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care composition may include a powder. The powder can be generally defined as dry, particulate matter having a particle size of 0.02-50 microns. The powder may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or combinations thereof. The powder may be surface treated with lecithin, amino acids, mineral oil, silicone oil, or various other agents either alone or in combination, which coat the powder surface and render the particles hydrophobic in nature.

The powder can also include or be an organic and/or inorganic pigment. Organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a combination with colored pigments, or some organic dyes, generally used as a combination with colored pigments and commonly used in the cosmetics industry, can be added to the composition.

In general, these coloring agents can be present in an amount by weight from 0 to 20% with respect to the weight of the personal care composition.

Pulverulent inorganic or organic fillers can also be added, generally in an amount by weight from 0 to 40% with respect to the weight of the personal care composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked. The fillers may typically be present in a proportion of from 0 to 35% of the total weight of the composition, more typically 5 to 15%. Mention may be made in particular of talc, mica, silica, kaolin, nylon powders (in particular ORGASOL), polyethylene powders, Teflon, starch, boron nitride, copolymer microspheres such as EXPANCEL (Nobel Industrie), polytrap and silicone resin microbeads (TOSPEARL from Toshiba, for example).

The personal care composition may include a sunscreen. Sunscreens typically absorb ultraviolet light between 290-320 nanometers (the UV-B region) such as, but not exclusively, para-aminobenzoic acid derivatives and cinnamates such as octyl methoxycinnamate and those which absorb ultraviolet light in the range of 320-400 nanometers (the UV-A region) such as benzophenones and butyl methoxy dibenzoylmethane. Some additional examples of sunscreens are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. In various embodiments, the sunscreen is as described in EP-A-678,292, which is expressly incorporated herein by reference in one or more non-limiting embodiments. In various embodiments, sunscreens include at least one carboxylic or better still sulphonic acid radical. This acid radical can be in free form or in partially or totally neutralized form. It is possible to use one or more hydrophilic screening agents containing acid functionality. As examples of acidic screening agents containing at least one $SO_3H$ group, mention may be made more particularly of 3-benzylidine-2-camphorsulphonic derivatives. A particularly typical compound is benzene-1,4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl) benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy) benzylidenecamphor-10-sulphonic acid, 3-(4-methoxy) benzylidenecamphor-10-sulphonic acid, 3-(4,5-dimethoxy) benzylidenecamphor-10-sulphonic acid, 3-(4-n-butoxy) benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597, and FR 2,236,515, 2,282,426, 2,645,148, 2,430,938 and 2,592,380, each of which is expressly incorporated herein by reference in one or more non-limiting embodiments. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by Merck, benzene-1,4-di(benzimidazol-2-yl-5-sulphonic acid), benzene-1,4-di(benzoxazol-2-yl-5-sulphonic acid). The hydrophilic screening agent(s) can be present in the final composition according to the disclosure in a content which can be from 0.1 to 20%, typically from 0.2 to 10%, by weight relative to the total weight of the personal care composition.

Additional lipophilic screening agents can be utilized such as those derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607, each of which is expressly incorporated herein by reference in one or more non-limiting embodiments. 4-(tert-butyl)-4'-methoxydibenzoylmethane is currently sold under the trade name "Parsol 1789" by Givaudan. Another dibenzoylmethane derivative which is typical according to the present disclosure is 4-isopropyldibenzoylmethane, this screening agent being sold under the name "Eusolex 8020" by Merck. Similarly octocrylene, a liquid lipophilic screening agent that is already known for its activity in the UV-B range is commercially available, and is sold in particular under the name "Uvinul N 539" by BASF. As another lipophilic (or liposoluble) screening agent which can be used in the disclosure, mention may also be made of p-methylbenzylidenecamphor, which is also known as a UV-B absorber and is sold in particular under the trade name "Eusolex 6300" by Merck. The lipophilic screening agent(s) can be present in the composition according to the disclosure in a content which can be from 0.5 to 30%, typically from 0.5 to 20%, of the total weight of the composition. Other examples of lipophilic or hydrophilic organic screening agents are described in patent application EP-A-0,487,404, which is expressly incorporated herein by reference in one or more non-limiting embodiments. The cosmetic and/or dermatological compositions according to the disclosure can also include pigments or alternatively nanopigments (average primary particle size: generally between 5 nm and 100 nm, typically between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum stearate, and silicones. Such coated or uncoated metal oxide nanopigments are described in particular in patent applications EP-A-0,518,772 and EP-A-0,518,773, each of which is expressly incorporated herein by reference in one or more non-limiting embodiments.

A thickening agent may be utilized in the personal care composition to provide a convenient viscosity. For example, viscosities of from 500 to 25,000 mm$^2$/s at 25° C. or more alternatively of from 3,000 to 7,000 mm$^2$/s at 25° C. may be obtained. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or combinations of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in a shampoo composition, may provide a viscosity of from 500 to 25,000 mm$^2$/s at 25° C. Alternatively the thickening agent may be present in an amount from 0.05 to 10 wt % and alternatively 0.05 to 5 wt % based on the total weight of the personal care composition. Stabilizing agents can also be used, e.g. in a water phase of an emulsion. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to 0.1 to 5 wt % and more alternatively 0.5 to 3 wt % of the personal care composition. The hydrocolloids include gums, such as Xantham gum, carageenans, or Veegum and thickening agents, such as carboxymethyl cellulose. Polyols, such as glycerine, glycols, and sorbitols can also be used. Alternative polyols are glycerine, propylene glycol, sorbitol, and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Referring back, the emulsion can be used in anti-perspirant and deodorant compositions under but not limited to the form of sticks, soft solid, roll on, aerosol, and pumpsprays. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The personal care composition can be an aerosol in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions may also be included in the personal care compositions. For example, such silicones include silicone fluids, gums, resins, elastomers; silicone surfactants and emulsifiers such as silicone polyethers, organofunctional silicones such as amino functional silicones and alkylmethylsiloxanes. Alkylmethylsiloxanes may be included in the present compositions. These siloxane polymers generally typically have the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. Both the volatile and liquid species of alkylmethysiloxanes can be used in the composition.

Silicone gums other than those described above may also be included in the personal care compositions. Suitable non-limiting gums include insoluble polydiorganosiloxanes having a viscosity in excess of 1,000,000 centistoke (mm$^2$/s) at 25° C., alternatively greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke (mm$^2$/s) at 25° C. up to 20 million centistoke (mm$^2$/s) at 25° C. Compositions of this type in are described for example in U.S. Pat. No. 6,013,682, which is expressly incorporated herein by reference in one or more non-limiting embodiments.

Silicone resins may also be included in the personal care composition. These resins are generally highly crosslinked polymeric siloxanes. Crosslinking is typically obtained by incorporating trifunctional and/or tetrafunctional silanes with the monofunctional silane and/or difunctional silane monomers used during manufacture. The degree of crosslinking required to obtain a suitable silicone resin will vary according to the specifics of silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be used. Commercially available silicone resins suitable for applications herein are generally supplied in an unhardened form in low viscosity, volatile or nonvolatile silicone fluids. The silicone resins may be incorporated into compositions of the disclosure in their non-hardened forms rather than as hardened resinous structures.

Silicone carbinol fluids may be included in the personal care composition. These materials can be commonly described as substituted hydrocarbyl functional siloxane fluids or resins and some are described in WO 03/101412 A2, which is expressly incorporated herein by reference in one or more non-limiting embodiments.

Water soluble or water dispersible silicone polyethers may also be included in the personal care composition. These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

EXAMPLES

A series of dispersions/emulsions and particles are formed according to this disclosure, as described in detail below. Particle size of silicone rubber dispersion is determined by using a Malvern Mastersizer® S unless specifically described otherwise.

Example 1 (—Si(OMe)$_3$ Functional Particles)

50 g of a methylhydrogen/dimethyl polysiloxane fluid having a kinematic viscosity of 107 centistokes, an approximate degree of polymerization of 100 and a hydrogen content as Si—H of 0.083% is weighed into a 100 g max cup. This is followed by 1.80 g of 1,5-hexadiene and 0.5 g of the SiH compound: HSiMe$_2$OSiMe$_2$C$_2$H$_4$Si(OMe)$_3$ and two drops from a pipette corresponding to approximately of 0.2 g of a soluble Pt catalyst that is Pt divinyltetramethyldisiloxane complex in a vinyl functional siloxane (the catalyst composition having the equivalent of 0.5% elemental Pt). The mixture is spun for 15-30 seconds at maximum speed in a SpeedMixer® DAC-150.

0.7 g of a 70% aqueous solution of isohexadecyl alcohol (20) ethoxylate (Arlasolve® 200), 70% in water, is then added followed by 10.0 g of DI water (H$_2$O#1). The cup is spun at maximum speed in the DAC-150 SpeedMixer® for 10-120 seconds. The contents of the cup are inspected and the mixture is observed to have inverted into an o/w emulsion. The cup is spun again at maximum speed. The emulsion is then diluted with additional dilution water (H$_2$O#2) in three incremental water addition and mixing steps such that the total amount of dilution water (H$_2$O#2) that is added is 27 g. The sample is placed into a 40-75° C. oven for 2-6 hours. The cup is then cooled.

The particles are harvested by vacuum filtration using a Buchner funnel equipped with standard laboratory filter paper. The resulting filter cake, which includes silicone rubber particles, is washed with DI water during filtration. The filter cake is removed from the Buchner filter and placed into a glass dish and allowed to air dry at ambient laboratory conditions. The sample weight is monitored until the weight change is small to ensure that the sample is dry. The dried particles are transferred to a jar for storage. Particle size results from the light scattering measurement is as follows: mean (D$_v$50)=15 micrometers; 90% of particles less than (D$_v$90)=25 micrometers. This composition includes spherical particles of silicone elastomer having either —Si(OMe)$_3$ or —Si(OH)$_n$ (n=1, 2 or 3) groups attached thereto.

Example 2 (—Si(OMe)$_3$ Functional Particles; Particle Size: 7.5 Micrometer)

50 g of a methylhydrogen/dimethyl polysiloxane fluid having a kinematic viscosity of 100 centistokes, an approximate degree of polymerization of 100 and a hydrogen content as Si—H of 0.08% is weighed into a 100 g max cup. This is followed by 5.29 g of a vinyl-functional siloxane with the formula (Me2ViSiO)4Si having a viscosity of 3 centistokes and 1.0 g of the SiH compound: HSiMe$_2$OSiMe$_2$C$_2$H$_4$Si(OMe)$_3$ and two drops from a pipette corresponding to approximately of 0.2 g of a soluble Pt catalyst that is Pt divinyltetramethyldisiloxane complex in a vinyl functional siloxane (the catalyst composition having the equivalent of 0.5% elemental Pt). The mixture is spun for 15-30 seconds at maximum speed in a SpeedMixer® DAC-150.

0.76 g of lauryl alcohol (4) ethoxylate (Brij® 30) and 1.57 g of a 72% aqueous solution of lauryl alcohol (23) ethoxylate (Brij® 35L) is then added followed by 9.8 g of DI water (H$_2$O#1). The cup is spun at maximum speed in the DAC-150 SpeedMixer® for 10-120 seconds. The contents of the cup are inspected and the mixture is observed to have inverted into an o/w emulsion. The cup is spun again at maximum speed. The emulsion is then diluted with additional dilution water (H$_2$O#2) in 3-7 incremental water addition and mixing steps such that the total amount of dilution water (H$_2$O#2) that is added is 34 g. The sample is placed into a 40-75° C. oven for 2-6 hours. The cup is cooled and particle size of the resulting silicone rubber dispersion is determined using a Malvern Mastersizer® S. Particle size results from the light scattering measurement is as follows: mean (D$_v$50)=7.5 micrometers.

The particles are obtained and the same procedure in Example 1 was applied and dried. This composition includes spherical particles of silicone elastomer having either —Si(OMe)$_3$ or —Si(OH)$_n$ (n=1, 2 or 3) groups attached thereto.

Example 3 (Cationic Functional Particles)

Using the same procedure as described in Example 1, a dispersion of particles having —Si(OMe)$_3$ functionality is prepared. The particles are harvested and they are treated with a quaternary ammonium functional silane.

250 g of a methylhydrogen/dimethyl polysiloxane fluid having a kinematic viscosity of 107 centistokes, an approximate degree of polymerization of 100 and a hydrogen content as Si—H of 0.083% is weighed into a 500 g max cup. This is followed by 9.36 g of 1,5-hexadiene and 4.14 g of the SiH compound: HSiMe$_2$OSiMe$_2$C$_2$H$_4$Si(OMe)$_3$ and 8 drops from a pipette corresponding to approximately of 0.2 g of a soluble Pt catalyst that is Pt divinyltetramethyldisiloxane complex in a vinyl functional siloxane (catalyst composition having the equivalent of 0.5% elemental Pt). The mixture is spun for 15-30 seconds at maximum speed in a SpeedMixer® DAC-600.

3.0 g of lauryl alcohol (4) ethoxylate (Brij® 30) and 6.0 g of a 72% aqueous solution of lauryl alcohol (23) ethoxylate (Brij® 35L) are weighed into the cup followed by 65 g of deionized (DI) water (H$_2$O#1). The cup is closed and spun for 2 minutes at maximum speed (2350 RPM). Dilution water (H$_2$O#2) is added incrementally in approximately 45 g aliquots with a mixing step after each addition until a total of 141 g of H$_2$O#2 is added. The emulsion is transferred to an oven and held at 40-75° C. for 2-6 hours. The sample is removed from the oven and allowed to cool after which particle size is determined using a Malvern Mastersizer® S. The particles are harvested by vacuum filtration. Upon filtering, the filter cake of particles is washed with two aliquots of 250 g of DI water. The moist filter cake is transferred to a glass dish where it is allowed to dry at ambient laboratory conditions until the sample weight does not change significantly and may be considered dry.

The particles (233.58 g) are transferred to a 1 quart jar whereby 190 g of methanol is added and mixed with the particles to form a slurry. Next 4.67 g of a 50% solution of n-octadecyldimethyl[3-trimethoxysilylpropyl] ammonium chloride in methanol and diluted in 15 g of additional methanol is added to the slurry contained in the jar. The jar is capped and the slurry is shaken vigorously for 1-2 minutes after which it is rolled on a jar roller for 1-2 hours. The contents of the jar are discharged into a clean glass dish and the methanol is allowed to evaporate at ambient laboratory conditions in a ventilated hood for 20-36 hours. Some of the particles agglomerate into large pieces and these are broken up by gently pressing with a spatula or flat tool. The particles are dried further in a 40-75° C. oven for 1-4 hours and finally transferred to a jar for storage. This composition includes silicone elastomeric spherical particles approximately 30 micrometers particle size treated with 1% by weight quaternary ammonium functional silane.

Example 4 (Cationic Functional Particles)

Using the same procedure as described in example 2, 238.0 g of harvested and dried particles having —Si(OMe)$_3$ functionality are dispersed in 180 g of methanol. 2.38 g of a 50% solution of n-octadecyldimethyl [3-trimethoxysilyl-propyl] ammonium chloride in methanol further diluted in 20 g methanol is added to the slurried particles and the composition is vigorously shaken for about 1-5 minutes. The slurry is poured into a glass dish and allowed to dry in a ventilated fume hood at ambient conditions for 20-36 hours. Lumps are crushed lightly and the particles are dried in a 40-75° C. oven for 1-4 hours after which the particles are transferred to a glass jar for storage. These particles include approximately 30 micrometers size spherical silicone elastomeric particles treated with 0.5% by weight quaternary ammonium functional silane.

Example 5 (Cationic Functional Particles)

Using a similar procedure as described in example 2, 225.9 g of dried particles having —Si(OMe)$_3$ functionality are obtained from a preparation of 250 g of a methylhydrogen/dimethyl polysiloxane fluid having a kinematic viscosity of 107 centistokes, an approximate degree of polymerization of 100 and a hydrogen content as Si—H of 0.083%, 9.4 g of 1,5-hexadiene, 2.75 g of HSiMe$_2$OSiMe$_2$C$_2$H$_4$Si(OMe)$_3$ and 8 drops from a pipette corresponding to approximately of 0.2 g of a soluble Pt catalyst that is Pt divinyltetramethyldisiloxane complex in a vinyl functional siloxane (catalyst composition having the equivalent of 0.5% elemental Pt), 6.0 g of a 70% aqueous solution of isohexadecyl alcohol (20) ethoxylate (Arlasolve® 200), 70% in water, 65 g of H$_2$O#1 and 139 g H$_2$O#2. The harvested and dried particles are slurried with 180 g of methanol and 4.28 g of a 50% solution in methanol of (MeO)$_3$Si(CH$_2$)$_3$N$^+$Me$_3^-$Cl diluted further with 20 g of methanol is added. The slurry is shaken vigorously for about 1-5 minutes after which the slurry is poured into a glass dish and allowed to dry in a ventilated fume hood for 20-36 hours at ambient laboratory conditions. The lumps are broken up and the powder is dried further for 1-4 hours in a 40-75° C. oven. This material includes spherical silicone particles having a mean particle size of approximately 30 micrometers and treated with 1% by weight of the cationic silane (MeO)$_3$Si(CH$_2$)$_3$N+Me$_3^-$Cl.

Example 6 (Aminofunctional Particles)

Using the same procedure as described in example 2, 225.9 g of harvested and dried particles having —Si(OMe)$_3$ functionality are dispersed in 180 g of methanol. 2.26 g of N-(2-aminoethyl)-3-aminopropyltrimethoxysilane dissolved in 20 g of methanol is added to the slurried particles and the composition is vigorously shaken for about 1-5 minutes. The slurry is poured into a glass dish and allowed to dry in a ventilated hood at ambient conditions for 20-36 hours. Lumps are lightly crushed and the particles are dried in a 40-75° C. oven for 1-4 hours after which the particles are transferred to a glass jar for storage. These particles include approximately 30 micrometers size spherical silicone elastomeric particles treated with 1.0% by weight aminofunctional silane.

Example 7 (Disulfide Functional Particles)

Using a similar procedure as described in example 1, —Si(OMe)$_3$ functional particles are prepared and treated with 1% [(MeO)$_3$SiC$_2$H$_6$]$_2$S—S. 250 g of a methylhydrogen/dimethyl polysiloxane fluid having a kinematic viscosity of 107 centistokes, an approximate degree of polymerization of 100 and a hydrogen content as Si—H of 0.083% is weighed into a 500 g max cup. This is followed by 9.36 g of 1,5-hexadiene and 5.0 g of the SiH compound: HSiMe$_2$OSiMe$_2$C$_2$H$_4$Si(OMe)$_3$ and 8 drops from a pipette corresponding to approximately of 0.2 g of a soluble Pt catalyst that is Pt divinyltetramethyldisiloxane complex in a vinyl functional siloxane (catalyst composition having the equivalent of 0.5% elemental Pt). The mixture is spun for 15-30 seconds at maximum speed in a SpeedMixer® DAC-600.

3.1 g of a 70% aqueous solution of isohexadecyl (20) ethoxylate (Arlasolve®200) is weighed into the cup followed by 90 g of deionized (DI) water (H$_2$O#1). The cup is closed and spun for 2 minutes at maximum speed (2350 RPM). Dilution water (H$_2$O#2) is added incrementally in approximately 40 g aliquots with mixing steps between additions until a total of 121 g of H$_2$O#2 is added. The composition is placed into a 40-75° C. oven for 2-6 hours. Particle size is measured after the emulsion cools.

Using the same procedure as described in example 2, particles are harvested, dried, slurried with methanol and 1% by weight of the particles of the sulfidosilane [(MeO)$_3$SiC$_2$H$_6$]$_2$S—S in 20 g of methanol is added. The slurried particles are treated and dried using the same procedure as described in Example 2. The dried and collected final composition includes approximately 50 micrometers spherical silicone particles treated with 1% of the disulfidosilane [(MeO)$_3$SiC$_2$H$_6$]$_2$S—S.

Example 8 (Tetrasulfide Functional Particles)

Using the same procedure as described in Example 6, a composition is prepared that includes approximately 50 micrometers spherical silicone particles treated with 1% of the tetrasulfidosilane [(MeO)$_3$SiC$_2$H$_6$]$_2$S—S—S—S.

Example 9 (Cationic Particles)

Using a similar procedure as described in Example 1, particles having —Si(OMe)$_3$ functionality are prepared. These particles are treated with a cationic silane in water. 250 g of a methylhydrogen/dimethyl polysiloxane fluid having a kinematic viscosity of 107 centistokes, an approximate degree of polymerization of 100 and a hydrogen content as Si—H of 0.083% is weighed into a 100 g max cup. This is followed by 9.36 g of 1,5-hexadiene and 5.0 g of the SiH compound: HSiMe$_2$OSiMe$_2$C$_2$H$_4$Si(OMe)$_3$ and 8 drops from a pipette corresponding to approximately 0.2 g of a soluble Pt catalyst that is Pt divinyltetramethyldisiloxane complex in a vinyl functional siloxane (the catalyst composition having the equivalent of 0.5% elemental Pt). The mixture is spun for 10-30 seconds at maximum speed (2350 RPM) in a SpeedMixer® DAC-600.

Next 3.13 g of a 70% aqueous solution of isohexadecyl alcohol (20) ethoxylate (Arlasolve® 200), 70% in water, is added followed by 70.0 g of DI water (H$_2$O#1). The cup is spun at maximum speed in the DAC-600 SpeedMixer® for 2 minutes. A total of 142 g of H$_2$O#2 is added to the cup in 3 increments with brief mixing after each addition. After the final addition and spinning, the contents of the cup are transferred to a 1 quart jar and placed into a 40-75° C. oven. After 2-6 hours in the oven, the jar is removed and the contents are allowed to cool to room temperature. Particle size is measured and found to be approximately 35 micrometers (mean). 2.64 g of a 50% solution of n-octadecyldimethyl [3-trimethoxysilylpropyl] ammonium chloride in methanol is dissolved in 20 g of DI water and the resulting solution is added to the aqueous dispersion of —Si(OMe)$_3$ functionalized silicone particles. The emulsion is shaken by hand for about 2-5 minutes and rolled on a jar roller for 1-3 hours after which the composition is filtered using a vacuum filter. The filter cake is washed with DI water and then transferred to a glass dish. The particles are allowed to dry at ambient laboratory conditions for 20-36 hours after which they are dried in a 30-50° C. oven for 1-4 hours until the sample weight does not change significantly.

This composition includes spherical silicone particles approximately 17 micrometers in diameter treated with 0.5% of (MeO)$_3$Si(CH$_2$)$_3$N$^+$Me$_2$C$_{18}$H$_{37}$-Cl. This composition differs from that of example 2 in that the silane is added to the particles in an aqueous medium whereby the composition of example 2, silane and particles are combined in a non-aqueous, methanolic slurry.

Example 10 Cationic Functional Particles in Ethanol Slurry

Using the same procedure as described in example 1, 53.9 g of harvested and dried particles having —Si(OMe)$_3$ functionality are transferred to a clean 100 g max cup whereby 20-50 g of 200 proof ethanol is added and mixed with the particles to form a slurry. Next 0.54 g of a 50% solution of n-octadecyldimethyl[3-trimethoxysilylpropyl] ammonium chloride in methanol is added to the slurry, mixed with a spatula by hand and then spun to mix thoroughly for 20-50 seconds. The slurry is discharged into a clean glass dish and the ethanol is allowed to evaporate at ambient laboratory conditions in a ventilated hood for 15-36 hours. Some of the particles agglomerate into large pieces and these are broken up by gently pressing with a spatula or flat tool. The particles are dried further in a 40-75° C. oven for 1-4 hours and finally transferred to a jar for storage. This composition includes silicone elastomeric spherical particles treated with 0.5% by weight quaternary ammonium functional silane.

The aforementioned Examples demonstrate how particles are formed from reactive siloxane components by emulsifying the components to form the particles and allowing the components within each particle to react to form particles of crosslinked siloxane polymers. The particles of crosslinked siloxane polymer also contain reactive groups on silicon such as alkoxy. The particles are further functionalized by combining them with organofunctional silanes and allowing the silanes to react with the particles through the alkoxy on silicon groups attached to the polymer within each particle. The end result is particles having organic functionality covalently bonded to their polymer networks.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

The invention claimed is:

1. A method of preparing particles in an emulsion wherein the particles have organic functionality disposed thereon, said method comprising the steps of:
   A. providing a first reactant having at least two unsaturated carbon-carbon moieties;
   B. providing a second reactant having at least two Si—H moieties, so long as the sum of the number of the unsaturated carbon-carbon moieties of the first reactant and the Si—H moieties of the second reactant is at least five and/or at least one of the unsaturated carbon-carbon moieties of the first reactant or the Si—H moieties of the second reactant is pendant;
   C. providing a third reactant having a silicon atom and a condensable reactive group bonded to the silicon atom and also having an unsaturated carbon-carbon moiety and/or a Si—H moiety;
   D. providing a hydrosilylation catalyst;
   E. providing a polar liquid;
   F. combining the first, second, and third reactants in the presence of the hydrosilylation catalyst and the polar liquid to form an emulsion wherein the first, second, and third reactants react via a hydrosilylation reaction to form particles in the emulsion that have a cross-linked network wherein the condensable reactive group is disposed on the particles, and wherein the particles are disposed in the polar liquid; and
   G. adding a silane to the particles wherein the silane has an organic moiety and a condensation leaving group such that the condensable reactive group of the particles reacts with the condensation leaving group of the silane via a condensation reaction to form the particles having the organic functionality disposed thereon.

2. The method of claim 1, wherein the step of combining the first, second, and third reactants further comprises phase inverting the combination of the first, second, and third reactants to form the emulsion.

3. The method of claim 1, wherein the third reactant has as the condensable reactive group at least one silicon-bonded alkoxy group.

4. The method of claim 1, wherein the third reactant is HSi(CH$_3$)$_2$OSi(CH$_3$)$_2$CH$_2$CH$_2$Si(OCH$_3$)$_3$ or H$_2$C=CHSi(OCH$_3$)$_3$.

5. The method of claim 4, wherein the third reactant is HSi(CH$_3$)$_2$OSi(CH$_3$)$_2$CH$_2$CH$_2$Si(OCH$_3$)$_3$.

6. The method of claim 1, wherein the condensable reactive group is an —Si(OR) group wherein R is an organic radical having 1-14 carbon atoms.

7. The method of claim 1, wherein the silane having the organic moiety and the condensation leaving group is a methoxy- and/or ethoxy-functional silane.

8. The method of claim 1, wherein the organic moiety of the silane comprises nitrogen or sulfur.

9. The method of claim 1, wherein the condensation leaving group is chosen from an alkoxy group, a carboxy group, an oxime group, an acetoxy group, an alkyleneoxy group, an amine group, or an amide group.

10. The method of claim 1, wherein the first reactant has two or more unsaturated carbon-carbon moieties and is free of silicon.

11. The method of claim 1, wherein the particles that have the condensable reactive group disposed thereon and the particles that have the organic functionality disposed thereon each independently have an average diameter of from 1 to 100 microns.

12. The method of claim 1, wherein the first reactant is a polydimethylsiloxane having one or two pendant unsaturated carbon-carbon moieties, the second reactant is a polydimethylsiloxane having one or two pendant Si—H moieties, and the third reactant is $HSi(CH_3)_2OSi(CH_3)_2CH_2CH_2Si(OCH_3)_3$ or $H_2C=CHSi(OCH_3)_3$.

13. A cross-linked particle formed from the method of claim 1.

14. A personal care composition comprising the cross-linked particle of claim 13.

15. A film comprising the cross-linked particles of claim 13.

16. A method of forming the film of claim 15, said method comprising the steps of:
    separating the polar liquid from the cross-linked particles; and
    forming the film from the cross-linked particles.

17. An emulsion comprising cross-linked particles and a polar liquid formed from the method of claim 1.

18. A method comprising separating from the emulsion of claim 17 the cross-linked particles from the polar liquid.

19. Cross-linked particles formed in accordance with the method of claim 18.

* * * * *